(12) United States Patent
Canioni et al.

(10) Patent No.: US 7,701,583 B2
(45) Date of Patent: Apr. 20, 2010

(54) COHERENCE SPECTROMETRY DEVICES

(75) Inventors: Lionel Canioni, Gradignan (FR);
Stéphane Santran, Gradignan (FR);
Bruno Bousquet, Gradignan (FR)

(73) Assignee: Centre National de la Recherche Scientifique—CNRS (FR)

( * ) Notice: Subject to any disclaimer, the term of this patent is extended or adjusted under 35 U.S.C. 154(b) by 325 days.

(21) Appl. No.: 11/664,244

(22) PCT Filed: Sep. 30, 2005

(86) PCT No.: PCT/FR2005/002420

§ 371 (c)(1),
(2), (4) Date: Jun. 12, 2007

(87) PCT Pub. No.: WO2006/037880

PCT Pub. Date: Apr. 13, 2006

(65) Prior Publication Data

US 2008/0117435 A1    May 22, 2008

(30) Foreign Application Priority Data

Oct. 1, 2004    (FR)    .................................. 04 52263

(51) Int. Cl.
*G01B 9/02* (2006.01)
*G01J 3/45* (2006.01)

(52) U.S. Cl. ...................................... 356/456; 356/455
(58) Field of Classification Search .................. 356/451, 356/455, 456
See application file for complete search history.

(56) References Cited

U.S. PATENT DOCUMENTS

| 4,183,669 | A | * | 1/1980 | Doyle | 356/451 |
| 4,652,130 | A | * | 3/1987 | Tank | 356/455 |
| 4,684,255 | A | * | 8/1987 | Ford | 356/455 |
| 5,148,235 | A | * | 9/1992 | Tank et al. | 356/455 |
| 5,777,736 | A | * | 7/1998 | Horton | 356/456 |
| 5,898,459 | A | * | 4/1999 | Smith et al. | 348/219.1 |
| 6,665,075 | B2 | * | 12/2003 | Mittleman et al. | 356/450 |
| 7,330,267 | B1 | * | 2/2008 | Weitzel | 356/456 |
| 7,502,117 | B1 | * | 3/2009 | Wickholm | 356/450 |
| 2003/0103209 | A1 | * | 6/2003 | Simon | 356/456 |

FOREIGN PATENT DOCUMENTS

| CA | 2 302 994 A1 | 9/2001 |
| GB | 712092 A | 7/1954 |
| JP | 57-44823 A | 3/1982 |

OTHER PUBLICATIONS

Jérôme Genest et al., "Throughput of tilted interferometers," Applied Optics, vol. 37, No. 21, Jul. 20, 1998.
John M. Harlander et al., "Spatial Heterodyne Spectroscopy for High Spectral Resolution Space-Based Remote Sensing", Optics and Photonics News, Jan. 2004, pp. 46-51.

* cited by examiner

*Primary Examiner*—Patrick J Connolly
(74) *Attorney, Agent, or Firm*—DLA Piper LLP (US)

(57) ABSTRACT

A spectrometry device comprising at least one wavefront-dividing interferometer comprising at least two unbalanced arms and at least one air wedge, a device for imaging interference fringes, an imaging sensor of the fringes and a processor that processes a signal derived from the sensor.

9 Claims, 8 Drawing Sheets

COHERENCE SPECTROMETRY DEVICES

RELATED APPLICATION

This is a §371 of International Application No. PCT/FR2005/002420, with an international filing date of Sep. 30, 2005 (WO 2006/037880 A1, published Apr. 13, 2006), which is based on French Patent Application No. 04/52236, filed Oct. 1, 2004.

TECHNICAL FIELD

The technology herein relates to the field of spectrometers, more particularly, to spectrometers that distinguish background noise from useful lines in spectrometric detection.

BACKGROUND

One of the problems encountered in this field may be found in the detection of fluorescence generated by a plasma. Indeed, a material, whether it is in solid, liquid or gaseous form may, after excitation by a laser pulse or any other excitation system, be transformed into plasma (mixture of free electrons, ions, atoms and molecules). If excitation of the material is significant enough, other well-known physical phenomena come into play such as cascade ionizations and collisions between free electrons. The effects increase the temperature of the plasma produced. The Bremsstrahlung of the moving electrons (inverse Brehmsstrahlung effect) therefore gives a white light emitted by the plasma. Analysis of the radiative deexcitation of the atoms and ions therefore allows the composition of the latter to be traced back via a spectral analysis of the light emitted by the plasma.

Detection and collection of fluorescence are conventionally carried out with an optical fiber placed at the level of the plume of the plasma. The spectrometers are therefore based on an optical design based on an echelette diffraction grating, an adjustable entrance slit, and spherical mirrors allowing the object and image points to be conjugated on a CCD camera. Reading software then allows the spectrum of light entering in the device to be displayed irrespective of the temporal or spatial coherence of the light. Thus, the incoherent light, emitted for example by Brehmsstrahlung radiation may distort the measurements and produce inaccuracies on the decisions. The method of "sorting" the emission spectrum from the incoherent white light is not satisfactory.

A number of publications disclose spectrometric methods by interferometry such as, for example, CA 2 302 994, but they have not tried to solve the problem of the incoherent white light.

An article from NASA published in the "Optics and Photonics News" journal in January 2004 describes a Fourier transform spectrometer based on a Michelson interferometer modified by replacing the mirrors with diffraction gratings. Such a spectrometer has a greater robustness to accelerations, but does not consider the problem of white light noise for detecting atomic lines.

SUMMARY

We provide a spectrometry device including at least one wavefront-dividing interferometer including at least two unbalanced arms and at least one air wedge, a device for imaging interference fringes, an imaging sensor of the fringes and a processor that processes a signal derived from the sensor.

We also provide a spectrometry device including a plurality of wavefront-dividing interferometers, each one of the interferometers including two unbalanced arms and at least one air wedge, a device for imaging interference fringes, an imaging sensor of the fringes and a processor that processes a signal derived from the sensor, imbalances between the two arms each one of the interferometer being different.

BRIEF DESCRIPTION OF THE DRAWINGS

Our technology will be better understood with the aid of the description, made hereafter purely by way of explanation, of selected representative structures, referring to the figures appended where.

DETAILED DESCRIPTION

Figure 1A:
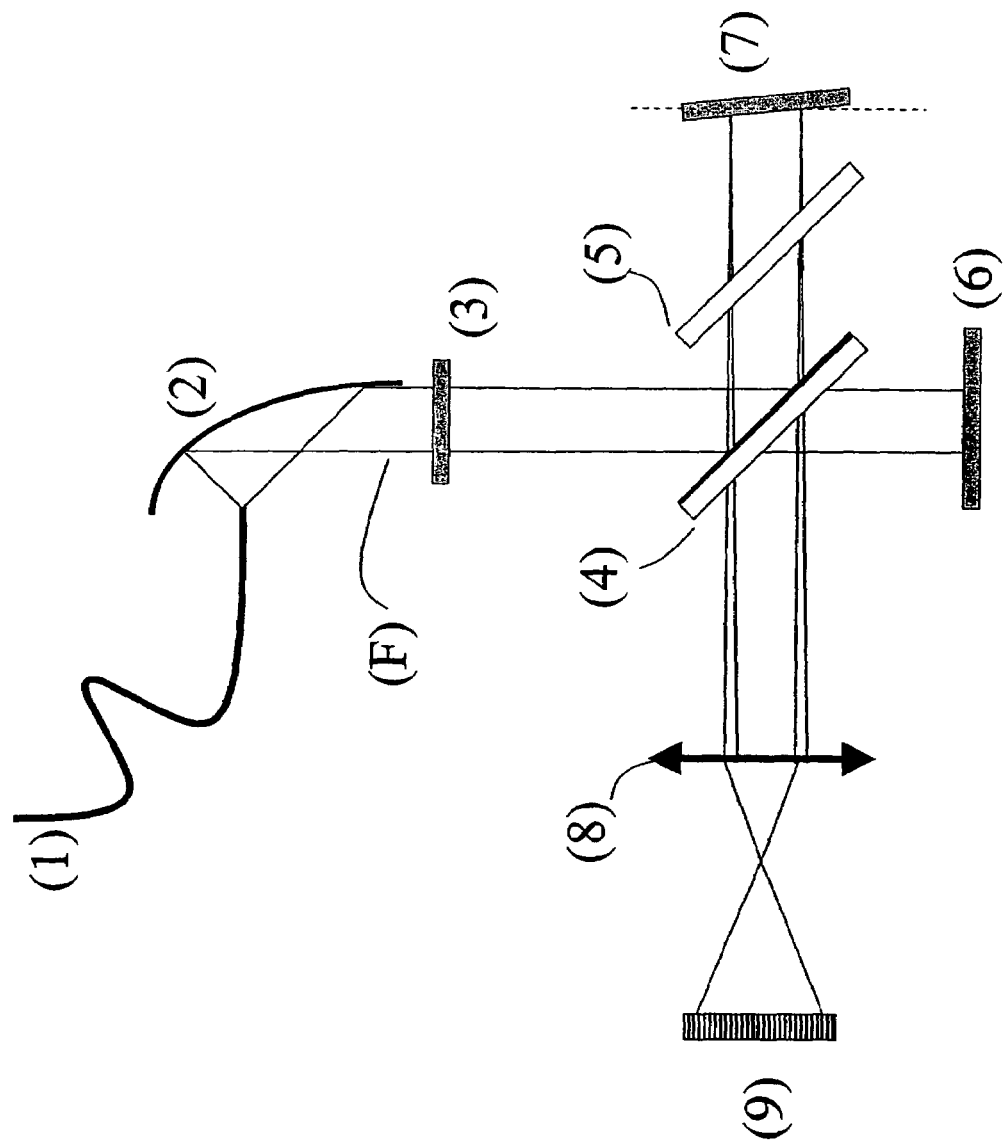
FIG. 1A is a schematic view showing a general diagram of a spectrometer.

It will be appreciated that the following description is intended to refer to specific examples of structure selected for illustration in the drawings and is not intended to define or limit the disclosure, other than in the appended claims.

We provide spectrometry devices that include at least one wavefront-dividing interferometer comprising at least two unbalanced arms and at least one air wedge, a device for imaging interference fringes, an imaging sensor of the fringes and means for processing a signal derived from the sensor.

It should be noted that generally, such a spectrometer allowing the incoherent light to be separated from the coherent light is called "coherence spectrometer" (15).

The imbalance introduced between the arms of the interferometer allows the temporal coherence to be taken into account and, therefore, the noise introduced by the incoherent white light to be eliminated.

It should be noted that for some applications, large spectral resolutions are necessary. A coherence spectrometer does not allow having a sufficient spectrum resolution, due to the number of pixels of the CCD, and the dimension of the optics. A particular combination of a plurality of coherence spectrometers, therefore, allows the resolution to be increased.

Illustrated in FIG. 1A, the spectrometer is, for example, used on an output of an optical fiber (1) and a mirror collimator (2) for detecting the line comprising an incoherent white light noise.

For example, it uses a Michelson interferometer with an air wedge.

It includes in a known way a beam splitter (4) and a compensating plate (5), a slightly inclined cylindrical mirror (7) and a non-inclined cylindrical mirror (6).

It must be understood that any interferometric device may be used if it is possible to introduce an imbalance in the arms of the latter. In particular, one skilled in the art can use Mach-Zehnder devices.

More specifically, in the case of the Michelson, the characteristics of the above described elements are as follows:
- the beam splitter (4) is a 50/50 beam splitter on a very large spectral width. It should be noted that this is possible by using a metallic process used for the metallic neutral density filters which allow having a transmission of (50%±5%) of 200 nm at more than 1 µm;
- the beam splitter (4) and the compensating plate (5) have a very good surface quality, so as not to damage the spatial quality of the beams, which would interfere with the interference fringes;
- the thicknesses of the beam splitters and compensating plates are as thin as possible (for example, on the order of a millimeter) to limit variations of the offset of the beams traversing them according to the wavelength.

The two arms of the Michelson, comprising the segments (cylindrical mirror (6)-beam splitter) and (cylindrical mirror (7)-beam splitter) are unbalanced, i.e. the lengths of the two segments are not equal. This causes a non null operating difference between the rays emitted by the two arms. The Michelson used is therefore a wavefront divider.

The operating difference allows incoherent light interferences (for example, emitted by Brehmsstrahlung effect) to be eliminated. Indeed, the operating difference between the rays derived from the delay between the two arms of the interferometer simulates two sources emitting incoherently: the sources therefore do not interfere.

The imbalance is adjustable to make it possible to adapt the level of coherence with the measurement without deteriorating the interferences.

The mirror (7) is inclined by approximately 0.2 degrees, which forms an air wedge between the two beams which interfere. Parallel interference fringes are therefore obtained and displayed on a wide CCD detector (9).

The CCD sensor may be chosen according to one direction, for example a line of 8,000 pixels, and the representation of the interfringes is obtained, on one hand, with the aid of a cylindrical doublet lens (8) in one direction for making the image of the fringes, and the cylindrical mirrors (6) and (7) in the other direction for focusing the beam according to a line.

The image obtained on the CCD sensor is then subjected to a mathematical process for recovering a fluorescence spectrum or more generally a set of lines. Those skilled in the art know such algorithms in the field of Fourier transform spectroscopy. The algorithms use the size and the contrast of the interference fringes obtained for determining the composition of the emission spectrum.

Moreover, it should be noted that the quality of the CCD sensor is important so that it is not saturated by the incoherent white light received. The typical spectral resolution obtained with the aid of a spectrometer is on the order of 1,000 with a 6,000 pixel sensor.

On the output of the spectrometer, and if the sensor is not saturated, it is therefore possible to determine the composition of the material analyzed.

Finally, it is advisable to note that elimination of incoherent light by the abovementioned device largely facilitates detection because the incoherent white light is included in the zero frequency peak. The latter is therefore eliminated by frequent processing.

Figure 1B:
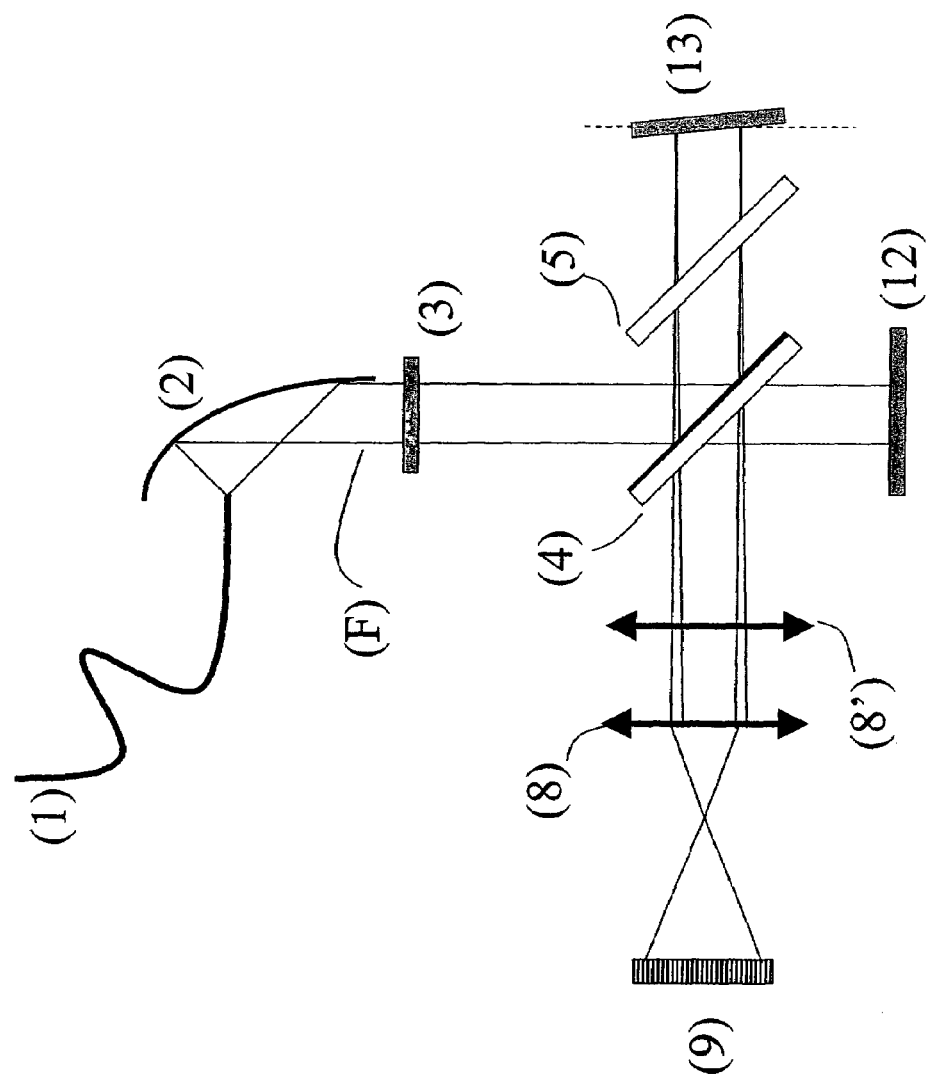
FIG. 1B is a schematic view showing another spectrometer.

FIG. 1B shows where the cylindrical mirrors (6) and (7) allowing the focusing of the beam in the CCD sensor (9), are replaced in a cylindrical lens (8'). Instead, the mirrors (6) and (7), are therefore placed a non-inclined plane mirror (12) and an inclined plane mirror (13).

Figure 2:
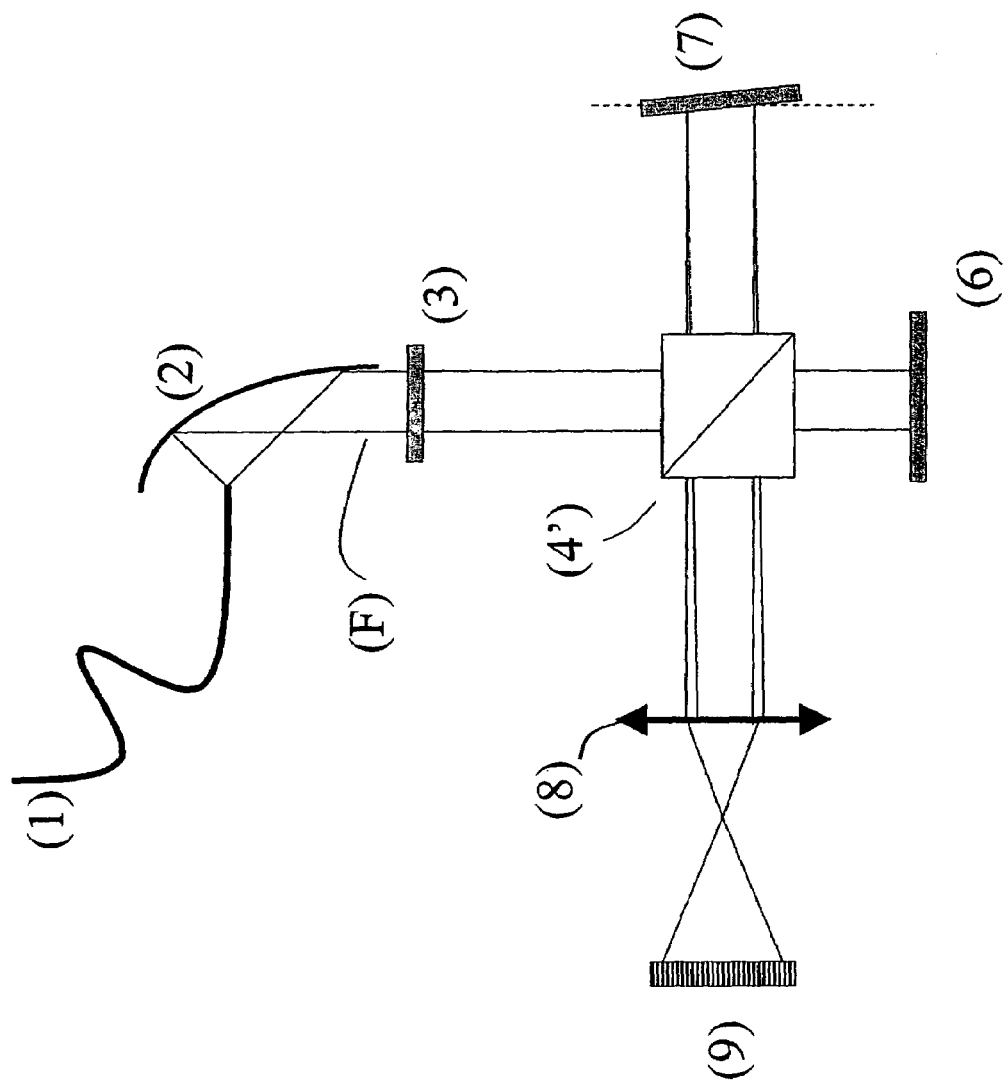
FIG. 2 is a schematic view showing yet another spectrometer.

FIG. 2 shows where the beam splitters and compensating plates are grouped into a single element (4').

Figure 3:
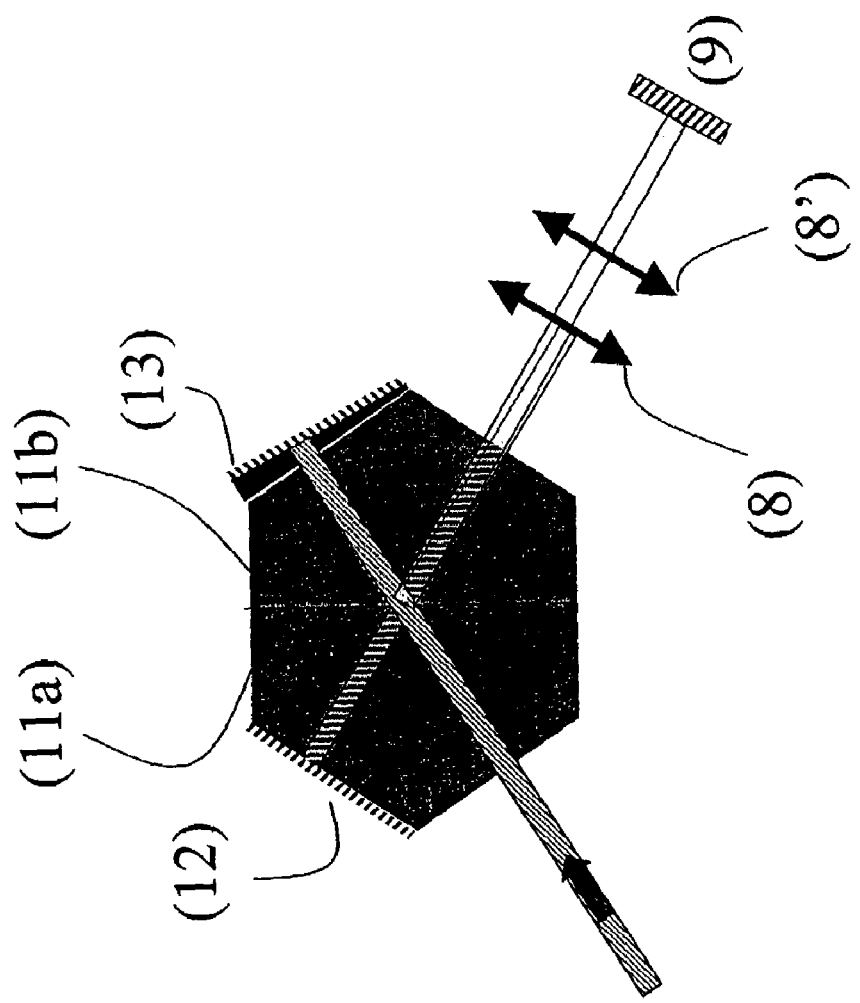
FIG. 3 is a schematic view showing a spectrometer in a compacted form.

A coherence spectrometer in a particularly compact form is illustrated in FIG. 3. According to that mode of use, the light beam is split and recombined within glued fused silica prisms (11a) and (11b), which reinforces the stability of the interferometric system. The plane mirrors (12) and (13) introduce the imbalance of the arms and the air wedge, and cylindrical lenses (8) and (8') allow the interference fringes to be imaged and to focus them, for example, on a line for the capture on a CCD camera (9). The spectral analysis of the fringes therefore allows the spectrum to be retrieved without being hindered by the incoherent light.

Figure 4:
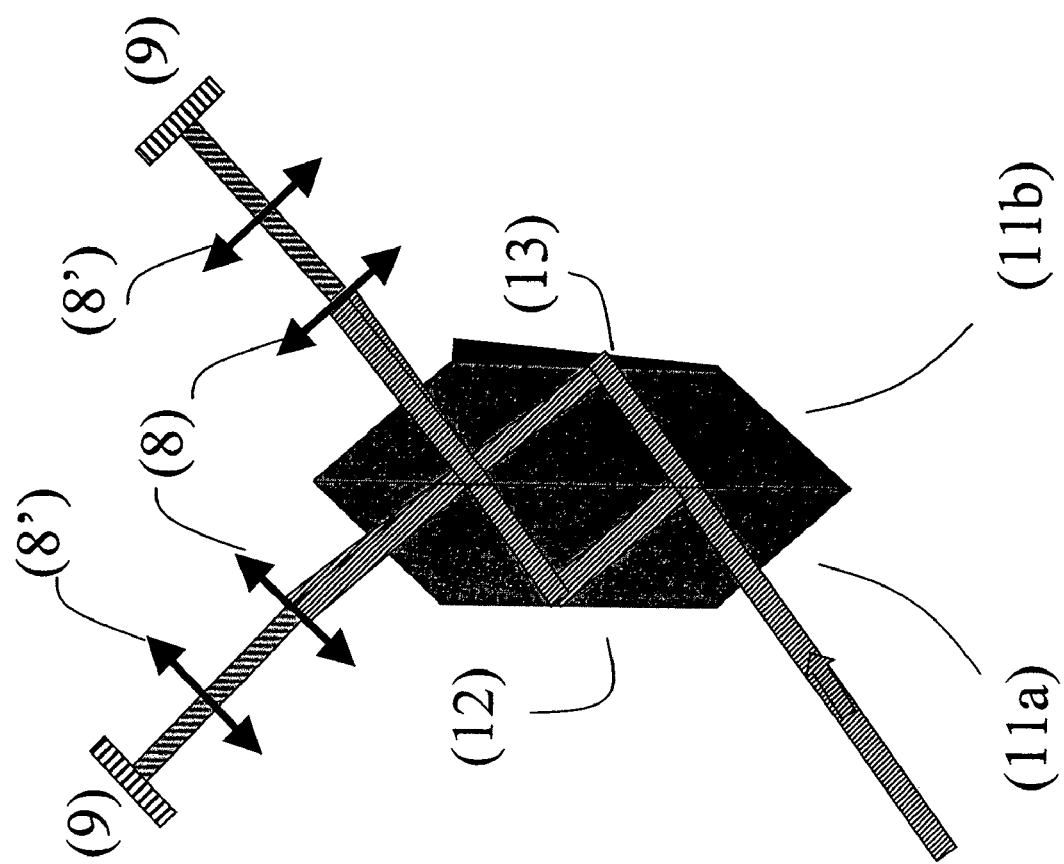
FIG. 4 is a schematic view showing another spectrometer in a compacted form.

FIG. 4 shows one other mode of use with possibly two CCD sensors for detecting the interfringes and a double splitting of the beams at the level of the fused silica prism.

Figure 5:
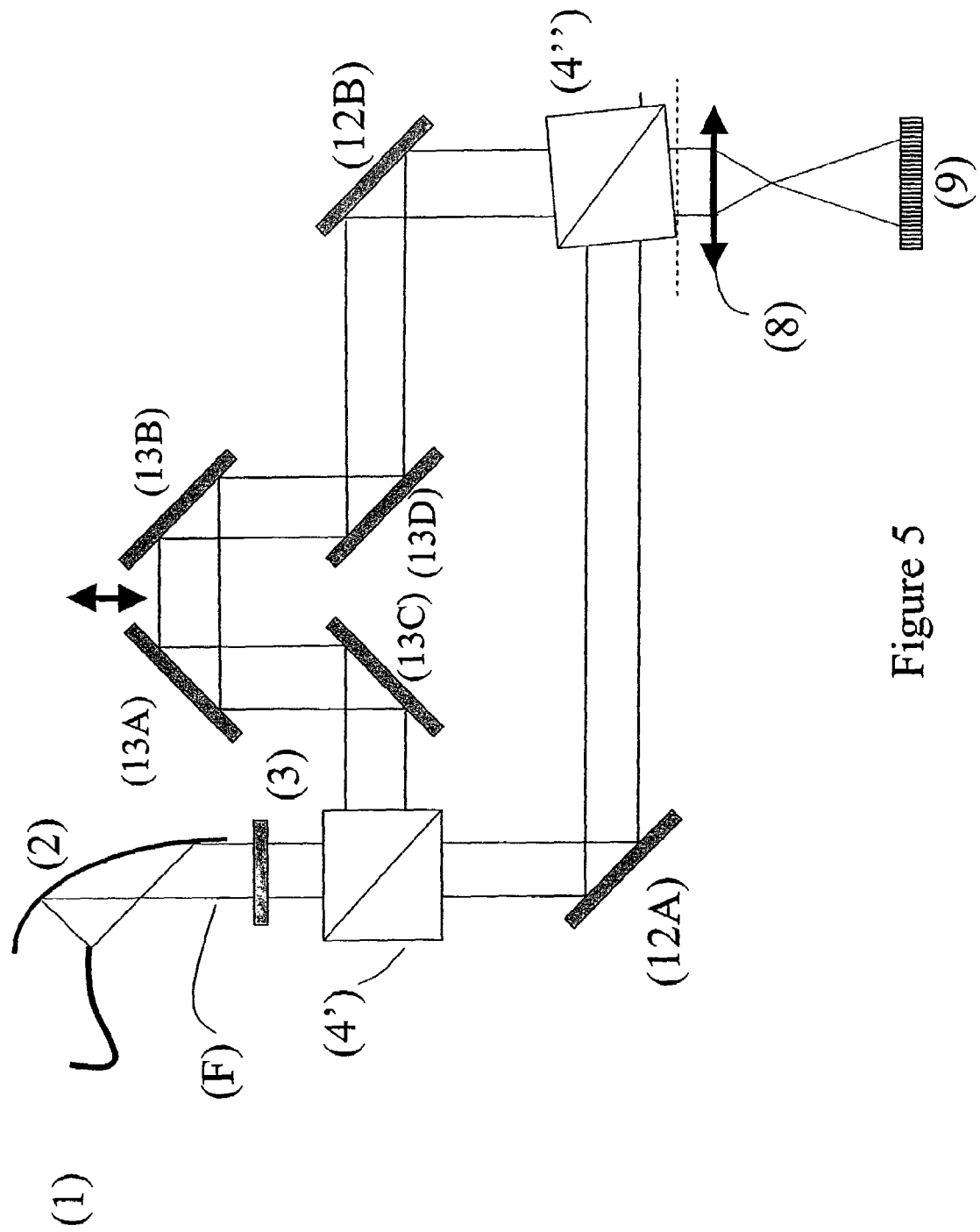
FIG. 5 is a schematic view showing a spectrometer in a Mach-Zehnder form.

FIG. 5 illustrates a case of a Mach-Zehnder interferometer. In that type of interferometer, the operating difference between the two arms of the interferometer is obtained by introduction of the mirrors 13 A, 13B, 13C and 13D. The beam splitter 4" therefore plays the role of air wedge for observing the interferences at the level of the sensor 9.

It is understood that the above structures are provided only by way of example and that many other structures and modes of use are possible for producing at least two unbalanced arms associated with an air wedge.

Finally, it should be noted that the spectroscopic devices may most particularly be used in fluorescence detection bringing into play the inverse Bremsstrahlung effect producing an incoherent white light by thermal agitation.

In that case, the device is installed as in FIG. 1A on the output of an optical fibre (1) allowing the fluorescence to be transported, after a mirror collimator (2).

In order to improve the resolution of the measuring instrument, it is also possible to combine a plurality of temporal coherence spectrometers as previously described.

Indeed, the use of a coherence spectrometer such as previously described allows one part of the interferogram to be acquired corresponding to the interference fringes recorded on the CCD sensor. The combination of a plurality of spectrometers with different retardations judiciously chosen therefore allows a plurality of parts of the interferogram to be acquired, and the resolution of the instrument to be increased.

Figure 6:
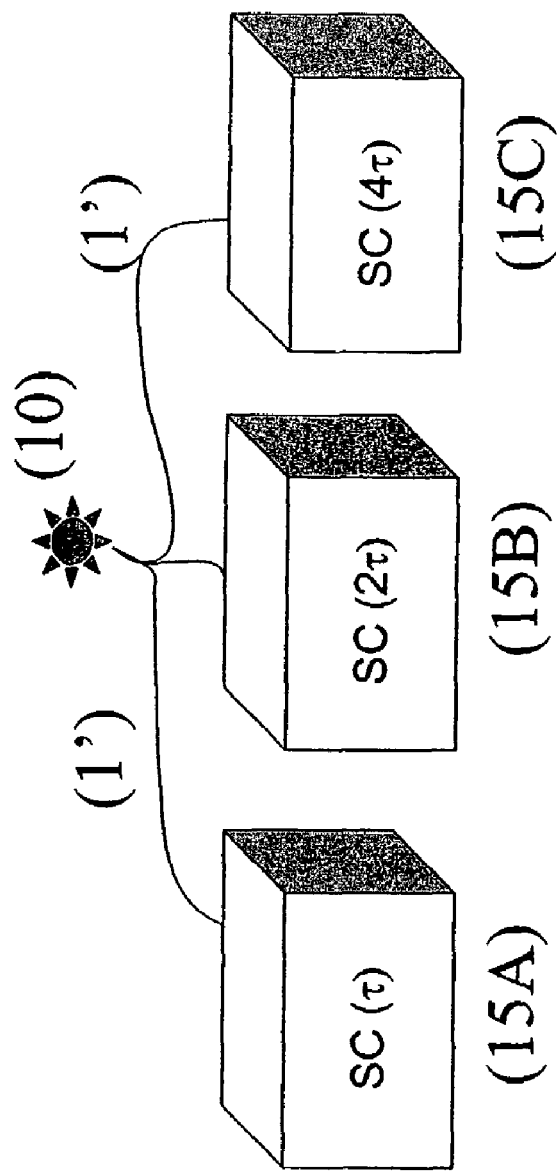
FIG. 6 is a schematic view showing a general diagram of a combination of three spectrometers.

Illustrated in FIG. 6, the spectrometer includes, for example, a divisible optical fibre (1') placed at the level of the plasma emission (10) which at the same time lights up a plurality of coherence spectrometers (15) having the imbalance adjustments of the optical trajectory between the arms different from one another.

For example, it uses a Michelson interferometer with an air wedge for the small imbalances, and a Mach-Zehnder interferometer for the large imbalances.

Indeed, the large imbalances of arm lengths may pose problems on a Michelson interferometer, due to the depth of field limitation on the imaging of interference fringes.

One method for obtaining the spectrum from the acquisition of a plurality of interferograms may be explained in the following way.

One algorithm for obtaining the spectrum is based on the Fourier transform. For a simple interferogram obtained with the aid of a single coherence interferogram, the calculation of the spectrum is well-known and carried out by simple Fourier transform followed by calculation of the magnitude. In the case of two combined coherence spectrometers 15A, 15B, the interferograms obtained are SC($\tau$) and SC($2\tau$), the interferograms corresponding to two coherence spectrometers of respective imbalances $\tau$ and $2\tau$. First, the complex Fourier transform of the first interferogram FFT(SC($\tau$)), then the complex Fourier transform of the sum of the two interferograms FFT(SC($\tau$)+SC($2\tau$)) is calculated. The spectrum derived from the combination of the two coherence interferometers is finally obtained by calculation of the magnitude of the multiplication of the preceding Fourier transforms:

ABS[FFT(SC($\tau$))*FFT(SC($\tau$)+SC($2\tau$))].

For a number of N coherence spectrometers (15A, 15B, 15C), the procedure is recursive. The imbalance between the arms of each coherence spectrometer added is double the previous. Thus, the interferogram of the third interferometer is written: SC($4\tau$). For example, the spectrum for three coherence spectrometers will be obtained with the aid of the formula:

ABS[FFT(SC(t))*FFT(SC(t)+SC(2t))*FFT(SC($\tau$)+SC(2t)+SC($4\tau$))].

By way of indication, the system of combinations of spectrometers may be compared with the aperture synthesis used in astronomy. In this case, the spectrometers cover various ranges of optical retardations, whereas in astronomy, the telescope mirrors cover various spatial apertures.

To improve the spectroscopic results, it is preferable, even by combining a plurality of coherence spectrometers to have CCD sensors with as many pixels as possible. This also allows the number of coherence spectrometers to be limited.

Figure 7:
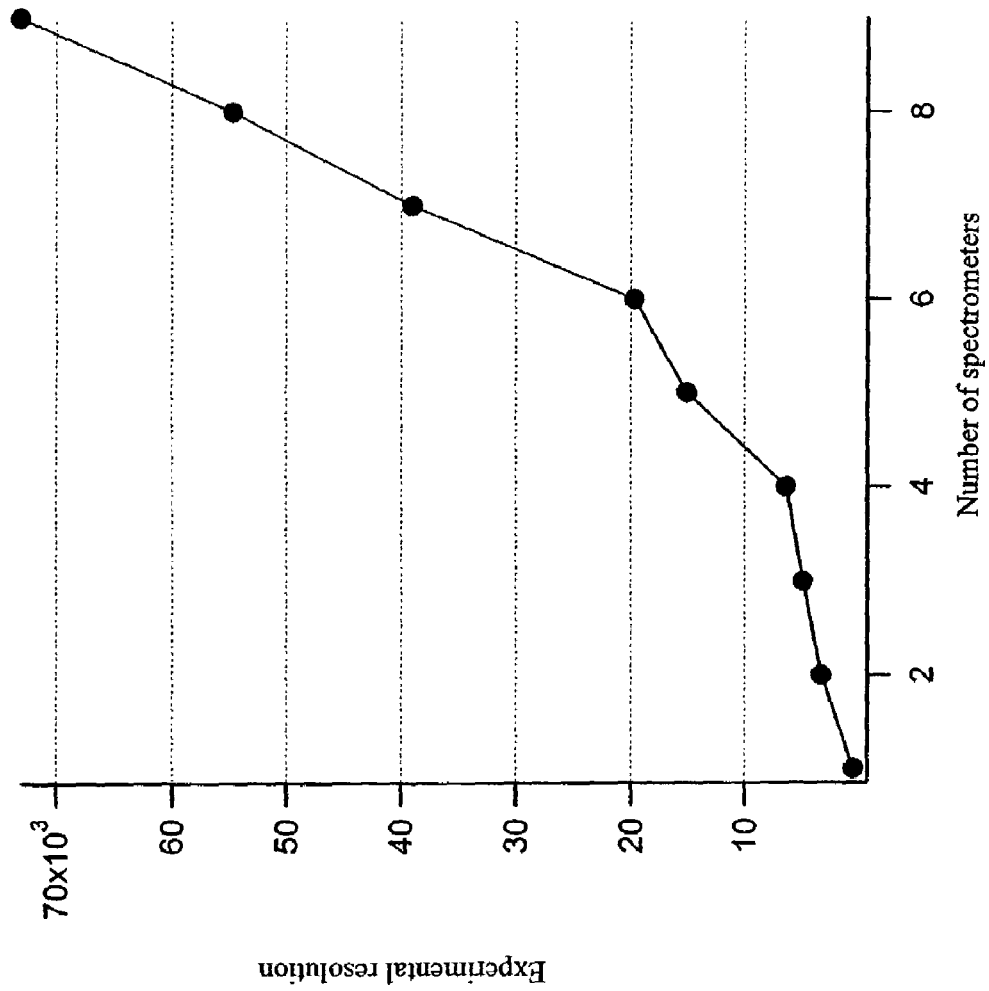
FIG. 7 is a graph of one experimental example of a development of the resolution according to the number of coherence spectrometers on one line of a neon helium laser.

FIG. 7 shows one experimental example of the development of the resolution according to the number of coherence spectrometers on one line of the neon helium laser. The resolution increases almost linearly according to the number of spectrometers. The curve was obtained with the aid of a CCD sensor with only 1,024 pixels. For the configuration with nine spectrometers, the line width measured is on the order of 9 picometers. A sensor wider than 6,000 pixels allows a resolution equivalent to more than 70,000 to be achieved with only 5 coherence spectrometers instead of 9.

The invention claimed is:

1. A spectrometry device that analyzes light comprising incoherent white noise comprising:
   at least one wavefront-dividing interferometer comprising
      1) at least two unbalanced arms comprising segments whose lengths are not equal and imbalance between the arms is adjustable to adapt temporal coherence levels by eliminating noise introduced by the incoherent white light, and 2) at least one air wedge,
   a device for imaging interference fringes;
   an imaging sensor of the fringes; and
   a processor that processes a signal derived from the sensor.

2. The spectrometry device according to claim 1, wherein an imbalance between the at least two arms is adjustable.

3. The spectrometry device according to claim 1, wherein the interferometer is of the Michelson type.

4. The spectrometry device according to claim 1, wherein the interferometer is of the Mach-Zehnder type.

5. The spectrometry device according to claim 1, wherein the processor uses an analysis by Fourier transform.

6. The spectrometry device according to claim 1, wherein the device for imaging fringes includes at least one cylindrical doublet lens for imaging the fringes.

7. The spectrometry device according to claim 1, wherein the imaging sensor is a CCD camera.

8. The spectrometry device according to claim 1, further comprising means for focusing the fringes to the sensor.

9. A spectrometry device that analyzes light comprising incoherent white noise comprising a plurality of wavefront-dividing interferometers, each one of the interferometers comprising:
   1) two unbalanced arms comprising segments whose lengths are not equal and imbalance between the arms is adjustable to adapt temporal coherence levels by eliminating noise introduced by the incoherent white light, and 2) at least one air wedge;
   a device for imaging interference fringes;
   an imaging sensor of the fringes; and
   a processor that processes a signal derived from the sensor, imbalances between the two arms each one of the interferometer being different.

* * * * *